United States Patent
Lei et al.

(10) Patent No.: US 8,987,449 B2
(45) Date of Patent: Mar. 24, 2015

(54) MEDICINE FOR TREATING ISCHEMIC BRAIN INJURY AND ITS SEQUELAE, AND PREPARATION METHOD THEREOF

(71) Applicants: Haimin Lei, Beijing (CN); Ying Hong, Beijing (CN)

(72) Inventors: Haimin Lei, Beijing (CN); Ying Hong, Beijing (CN)

(73) Assignee: Haimin Lei, Beijing (CN)

( * ) Notice: Subject to any disclaimer, the term of this patent is extended or adjusted under 35 U.S.C. 154(b) by 0 days.

(21) Appl. No.: 14/017,851

(22) Filed: Sep. 4, 2013

(65) Prior Publication Data

US 2014/0011813 A1  Jan. 9, 2014

Related U.S. Application Data

(63) Continuation of application No. PCT/CN2011/081528, filed on Oct. 28, 2011.

(30) Foreign Application Priority Data

Mar. 16, 2011 (CN) .......................... 2011 1 0062869

(51) Int. Cl.
*C07D 403/12* (2006.01)
*C07D 241/12* (2006.01)

(52) U.S. Cl.
CPC .................................. *C07D 241/12* (2013.01)
USPC ....................................................... 544/405

(58) Field of Classification Search
CPC .................................................... C07D 403/12
USPC ....................................................... 544/405
See application file for complete search history.

(56) References Cited

FOREIGN PATENT DOCUMENTS

| CN | 1079145 | 12/1993 | ............. A61K 31/11 |
| CN | 101143851 | 3/2008 | ........... C07D 241/12 |

OTHER PUBLICATIONS

A comparison of several modern alkylating agents—Lamoureux et al. ARKIVOC, 2009, (i), 251-264.*
Gretten et al., "Molecular therapy for the treatment of hepatocellular carcinoma," *Br. J. Cancer*, 100(1), pp. 19-23, Jan. 13, 2009.
Liu et al. (English Abstract within), "3D-QSAR study of novel ligustrazine derivatives," *Chinese Journal of Medicinal Chemistry*, vol. 17, No. 5, pp. 283-313, Oct. 2007.
Ribatti et al., "The chick embryo chorioallantoic membrane as a model for in vivo research on anti-angiogenesis," *Int. J. Dev. Biol.*, vol. 40, pp. 1189-1197 (1996).
State Intellectual Property Office of the P. R. China, International Search Report, International-Application No. PCT/CN2011/081528, dated Feb. 16, 2012, 4 pages.
Wang (English Abstract within), "Chemical modification of ligustrazine and bioactivity tests of Ligustrazine derivatives," *Chinese Doctoral Dissertations Full-text Database, Medicine and Health Sciences*, vol. 3, Issn. 1671-6779, 135 pages, Sep. 15, 2004.
Yang, "Research progress on the pharmacological effects of Ligustrazine," *Chinese Journal of Biochemical Pharmaceutics*, (03), pp. 215-217 (2010).
Yang (English Abstract), "Research progress on the pharmacological effects of Ligustrazine," *Chinese Journal of Biochemical Pharmaceutics*, (03), pp. 215-217 (2010).

* cited by examiner

*Primary Examiner* — Brian McDowell
(74) *Attorney, Agent, or Firm* — Nath, Goldberg & Meyer; Tanya E. Harkins; Joshua B. Goldberg

(57) ABSTRACT

Disclosed in the present invention are a compound of the general structure formula LQC-T as shown below, wherein R represents an aromatic organic acid or phenol or the structural analog thereof, such as protocatechuic acid, protocatechuic aldehyde, vanillic acid, gallic acid, caffeic acid, ferulic acid etc., and the synthesis and use of the compound. The compounds promote new blood vessel growth in the chick embryo chorioallantoic membrane, wherein LQC-T4 can be used to prepare a medicine for treating ischemic brain injury (stroke) and its sequelae.

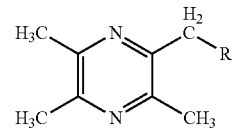

2 Claims, No Drawings

MEDICINE FOR TREATING ISCHEMIC BRAIN INJURY AND ITS SEQUELAE, AND PREPARATION METHOD THEREOF

CROSS REFERENCE

This is a continuation application of PCT/CN2011/081528 filed Oct. 28, 2011, which claims priority to Chinese Patent Application No. CN201110062869.5 filed Mar. 16, 2011, each of which is herein incorporated by reference.

TECHNICAL FIELD

The present invention relates to chemistry and bioscience filed, and specifically relates to the compound of LQC-T general structural formula and the synthesis and the use thereof. It is proved by pharmacological experiments that this kind of compound have the effect of promoting distinctly the growth of the new vessels of chicken chorioallantoic membrane, wherein LQC-T4 has significant medical effect in treating apoplexy caused by ischemic cerebral damage and the sequelae thereof. No toxic reaction is observed in 14 days by continuous observation when a maximum dosage of 5400 mg/kg LQC-T4 per day is administrated to mice and it can be seen that this medicine is of high safety and can be used to prepare a medicine for treating apoplexy caused by ischemic cerebral damage and the sequelae thereof

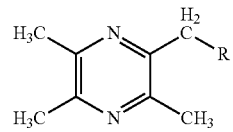

LQC-T general structural formula

R represents an aromatic organic acid or a phenol or a structural analog thereof, such as protocatechuic acid, protocatechualdehyde, vanillic acid, gallic acid, caffeic acid, ferulic acid, etc.

BACKGROUND ART

At present, regional cerebral ischemia, apoplexy and the sequelae thereof are the third biggest cause of death in developed country and are the main reason of disability of the grown-ups. Effective medicines in the early recovery phase of cerebral ischemia are rare at present. Thus, it is of great importance to develop a medicine having the effect of treating apoplexy caused by ischemic cerebral damage and having the effect enable to recover the motor function of the limbs after cerebral ischemic apoplexy. Many clinically effective anti-cerebrovascular ischemic damage Chinese traditional medicine compounds such as HuaTuoZaiZao pills, XiaoShuanTongLuo tablets, ShuXin oral liquid, LeMai granules, NaoDeSheng pills etc., all include Rhizoma ligustici chuanxiong. Tetramethylpyrazine, which is one of the main active components of Rhizoma ligustici chuanxiong, has extensive activity, such as antioxidation effect and calcium antagonistic effect, for cerebral vascular, and can regulate the unbalanced state of $TXA_2/PGI_2$, inhibit blood platelet conglomeration and lower blood pressure so that it has the effect of dilating vessels and inhibitting thrombus (YangXuemei, Research development of the pharmaceutical action of the Tetramethylpyrazine, [J] Chinese Journal of Biochemical Pharmaceutics, 2010, (03):215-217).

According to statistical data, there are 86 kinds of conventional Chinese traditional medicines used in ischemic apoplexy, wherein the most frequently used medicines are Rhizoma ligustici chuanxiong, Radices salviae miltiorrhizae, etc. The main active components of Radices salviae miltiorrhizae are compounds of the small molecule phenolic acid type. The present invention applies the medicine combination, selects the classic couplet medicines to combine the active components of Rhizoma ligustici chuanxiong and Radices salviae miltiorrhizae and provides a synthesis method of the medicine LQC-T for treating apoplexy caused by ischemic cerebral damage and the sequelae thereof and use thereof.

The present invention screens out a type of compound which is novel in structural skeleton, with definite activity, safe and low toxicity, and relatively definite target, from hundreds of natural compounds with modified structure, based on CAM model (Ribatti D, Vacca A, et al. The chick embryo chorioallantoic membrane as a model for in vivo research on anti-angiogenesis. Curr Pharm Biotechnol. 2000 July; 1(1): 73-82) and VEGF (Gretten T F, Korangy F, et al. Molecular therapy for the treatment of hepatocellular carcinoma. Br J. Cancer. 2009 Jan. 13; 100(1):19-23) screening and names it LQC-T.

SUMMARY OF THE INVENTION

The fist aim of the present invention is to provide compounds of the general structural formula (formula 1) of LQC-T.

The second aim of the present invention is to provide a synthesis route of LQC-T.

The third aim of the present invention is to provide a use of LQC-T in treating apoplexy caused by ischemic cerebral damage and the sequelae thereof

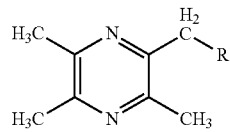

Formula 1

LQC-T general structural formula

R represents an aromatic organic acid or a phenol or a structural analog thereof, such as protocatechuic acid, protocatechualdehyde, vanillic acid, gallic acid, caffeic acid, ferulic acid, etc.

The aims of the present invention can be achieved by the following means.

A method for synthesizing LQC-T, comprising the following steps:

(1) dissolving protocatechuic acid into an organic solvent to react with bromotetramethylpyrazine in the presence of a catalyst at a certain temperature to generate LQC-T1 (compound 1: LQC-T1);

(2) dissolving protocatechuic acid into an organic solvent to react with bromotetramethylpyrazine in the presence of a catalyst at a certain temperature to generate LQC-T2 (compound 2: LQC-T2);

(3) dissolving vanillic acid into an organic solvent to react with bromotetramethylpyrazine in the presence of a catalyst at a certain temperature to generate LQC-T3 (compound 3: LQC-T3);

(4) dissolving vanillic acid into an organic solvent to react with bromotetramethylpyrazine in the presence of a catalyst at a certain temperature to generate LQC-T4 (compound 4: LQC-T4);

(5) dissolving protocatechualdehyde into an organic solvent to react with bromotetramethylpyrazine in the presence of a catalyst at a certain temperature to generate LQC-T5 (compound 5: LQC-T5);

(6) dissolving caffeic acid into an organic solvent to react with bromotetramethylpyrazine in the presence of a catalyst at a certain temperature to generate LQC-T6 (compound 6: LQC-T6); the reaction formulas of steps (1), (2), (3), (4), (5) and (6) in the above method are as follows:

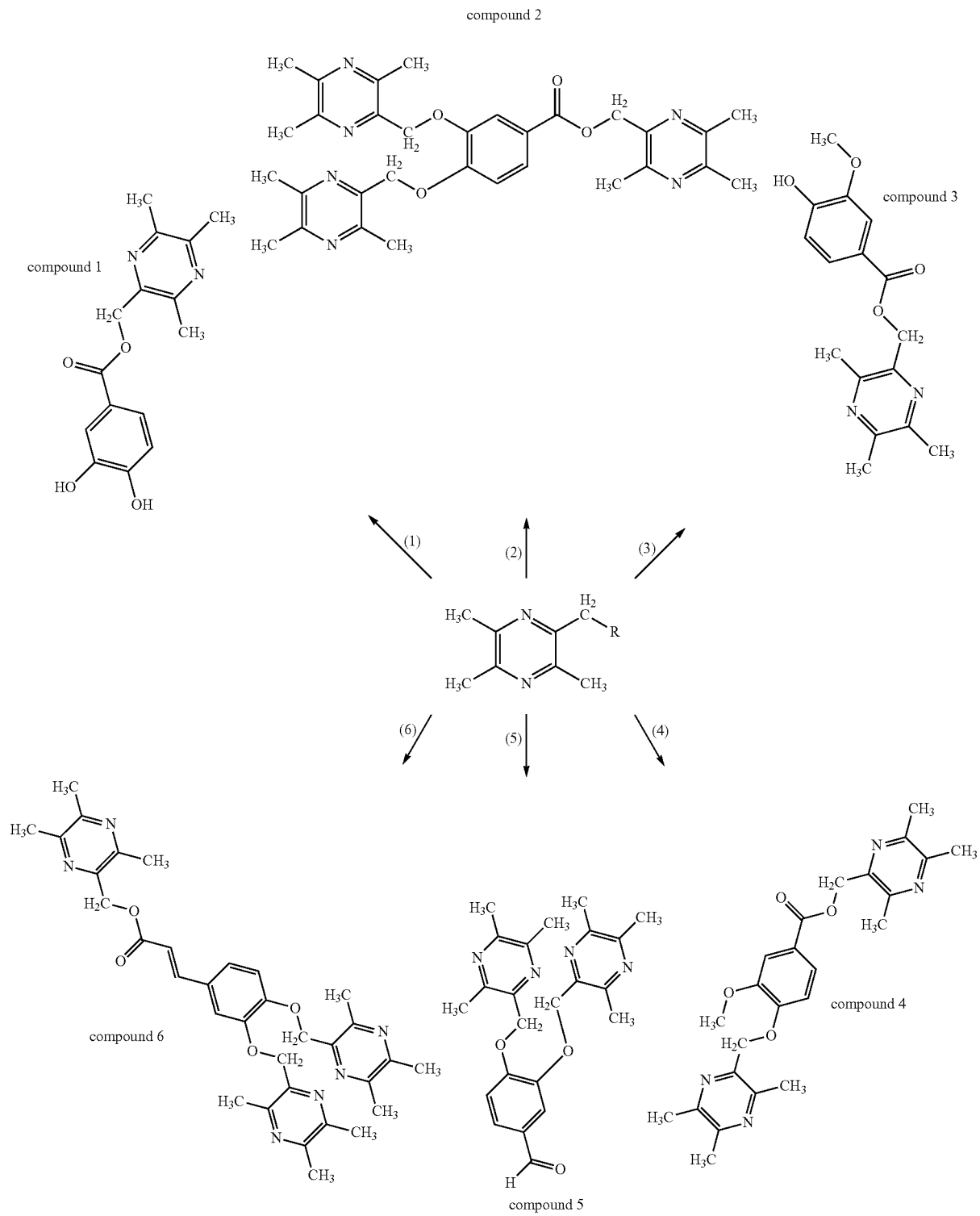

(1) In said method for synthesizing LQC-T, the organic solvent used is ether, alcohol, alkane, aromatic hydrocarbon, ketone, halogenated alkane, amide, nitrile and ester having 1-20 carbon atoms or mixture thereof at all kinds of ratios; the temperature is −20° C. to 250° C.; the catalyst is inorganic alkali or organic alkali wherein a representative of the inorganic alkali is kalium carbonate and a representative of the organic alkali is triethylamine; the reaction system needs inert gas protection.

(2) In said method for synthesizing LQC-T, wherein the mole ratio of protocatechuic acid to bromotetramethylpyrazine and the mole ratio of caffeic acid to bromotetramethylpyrazine are 1:(3-10) when LQC-T2, LQC-T4, LQC-T5, LQC-T6 are prepared.

(3) The synthesized LQC-T has an obvious activity of promoting the growth of the new vessels of CAM.

(4) The synthesized LQC-T 4 (compound 4) can promote growth of primary neuronal cells in an obvious way and ameliorate notably the neural function damage of rats after cerebral ischemia.

(5) When the synthesized LQC-T 4 (compound 4) is administrated at a maximum dosage of 5.4 g/kg per day to a mouse, no toxic or side effect is observed in 14 days.

(6) The synthesized LQC-T can be prepared into a oral formulation, an injection or an external formulation used in treating the diseases concerning apoplexy caused by ischemic cerebral damage and the sequelae thereof.

The present invention also provides a compound represented by the following general formula 2 or the pharmaceutically acceptable salt thereof, formula 2

Wherein, $R_1$ is hydrogen or a linear or branched $C_1$-$C_5$ alkyl which is substituted by pyrazine substituted by one or more alkyls, $R_2$ is hydrogen or a linear or branched $C_1$-$C_5$ alkyl which is substituted by pyrazine substituted by one or more alkyls, $R_1$ and $R_2$ are the same or different, $R_3$ is a linear or branched $C_1$-$C_5$ alkoxycarbonyl which is substituted by pyrazine substituted by one or more alkyls, an alkenyl substituted by a linear or branched $C_1$-$C_5$ alkoxycarbonyl which is substituted by pyrazine substituted by one or more alkyls, an aldehyde group.

Wherein $R_1$ is an alkyl which is substituted by pyrazine substituted by multiple methyls, $R_2$ is an alkyl which is substituted by pyrazine substituted by multiple methyls, $R_1$ and $R_2$ are the same or different, $R_3$ is an alkoxycarbonyl which is substituted by pyrazine substituted by multiple methyls, an alkenyl substituted by alkoxycarbonyl which is substituted by pyrazine substituted by multiple methyls, an aldehyde group.

Wherein $R_1$ is a pyrazine methylene substituted by three methyls, $R_2$ is a pyrazine methylene substituted by three methyls, $R_1$ and $R_2$ are the same or different, $R_3$ is a pyrazine methyleneoxy carbonyl which is substituted by three methyls, an alkenyl substituted by alkoxycarbonyl which is substituted by pyrazine substituted by multiple methyls, an aldehyde group.

The present invention also provides the following compounds:

1) (3,5,6-trimethylpyrazin-2-yl)methyl 4-hydroxy-3-methoxybenzoate, 2) (3,5,6-trimethylpyrazine-2-yl)methyl-3,4-bis((3,5,6-trimethylpyrazine-2-yl)methoxy) benzoate, 3) (3,5,6-trimethylpyrazine-2-yl)methyl-3-methoxy-4-hydroxybenzoate, 4) (3,5,6-trimethylpyrazine-2-yl)methyl 3-methoxy-4-((3,5,6-trimethylpyrazine-2-yl)methoxy) benzoate, 5) 3,4-bis((3,5,6-trimethylpyrazine-2-yl)methoxy)benzaldehyde, 6) (E)-(3,5,6-trimethylpyrazine-2-yl)methyl-3-(3,4-bis(3,5,6-trimethylpyrazine-2-yl)methoxy) phenyl)acrylate.

The present invention provides a method for synthesizing said compounds, which comprises the following steps:

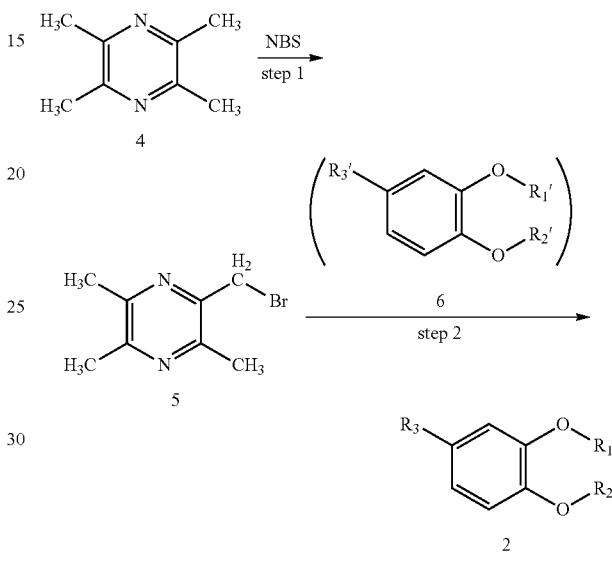

wherein $R_1$, $R_2$ and $R_3$ are as defined in formula 2, $R_1'$ and $R_2'$ are respectively selected from hydrogen or methyl, $R_3'$ is selected from hydroxyl, aldehyde group, carboxyalkyl and carboxyalkenyl, (1) reacting compound 4 with NBS (N-bromosuccimide) to obtain compound 5;

(2) reacting compound 5 with hydroxyl or carbonyl substituted benzene to obtain compound 2.

Wherein the step (1) is carried out in a solvent selected from tetrachloromethane, acetonitrile and dioxane.

Wherein step (1) includes adding a radical initiator.

Wherein the reaction in step (1) is carried out with the illumination of an incandescent lamp.

Wherein the reaction in step (2) is carried out in a solvent selected from xylene, acetone and N,N-dimethyl formamide.

Wherein the reaction in step (2) is carried out in the presence of a substance selected from triethylamine, kalium carbonate and piperidine.

Wherein the reaction in step (2) is carried out under heating.

Specifically, the method for synthesizing said compounds are as follows:

The preparation of
2-bromomethyl-3,5,6-trimethylpyrazine intermediate

Dissolving dehydrated tetramethylpyrazine into an organic solvent and adding NBS at a molar ratio of tetramethylpyrazine to NBS=1:(0.5-0.7), reacting for 10-12 h under reflux and after post-treatment purification, 2-bromomethyl-3,5,6-trimethylpyrazine being obtained as a pale-red half-oily substance;

Preferably, dissolving dehydrated tetramethylpyrazine into $CCl_4$, adding NBS at a molar ratio of tetramethylpyrazine to NBS=1:0.5, wherein adding a small amount of benzoylperoxide as the radical initiator is preferred, reacting for 10-12 h under reflux and after purification by post-treatment 2-bromomethyl-3,5,6-trimethylpyrazine being obtained as a pale-red half-oily substance;

More preferably, dissolving dehydrated tetramethylpyrazine into an organic solvent, preferably $CCl_4$, and adding NBS at a molar ratio of tetramethylpyrazine to NBS=1:0.7, adding a small amount of benzoylperoxide as the radical initiator, reacting with the illumination of an incandescent lamp and reacting for 10-12 h under reflux, then cooling and condensing the reaction liquid, and sucking away the excess tetramethylpyrazine under reduced pressure in 60-70° C. water bath, the residue being kept in a fridge for standing and thus 2-bromomethyl-3,5,6-trimethylpyrazine being obtained as a pale-red half-oily substance.

Synthesis of LQC-T1 (Compound 1)

Adding the prepared 2-bromomethyl-3,5,6-trimethylpyrazine and protocatechuic acid at a ratio of 1: (1-1.1) into a reaction solvent and then adding alkali, refluxing and agitating the reaction liquid for 11-14 h, stopping reaction until the raw materials are basically disappeared, post-treating and then separating the reaction liquid to obtain the compound 1;

Preferably, adding the prepared 2-bromomethyl-3,5,6-trimethylpyrazine and protocatechuic acid at a ratio of 1:1.05 into xylene, and then adding triethylamine, refluxing and agitating the reaction liquid for 13 h, wherein TLC is preferably used to detect the reaction; stopping reaction until the raw materials are basically disappeared, adding ethyl acetate to the reaction liquid and condensing it, and then dissolving the residue with a solvent, adding silica gel, evaporating the resultant sample to dryness at a reduced pressure and agitating, and eluting with benzene:acetone=(3-6):1 as the eluent to obtain a powder as compound 1;

More preferably, adding the prepared 2-bromomethyl-3,5,6-trimethylpyrazine and protocatechuic acid at a ratio of 1:1 into xylene, and then adding triethylamine, refluxing and agitating the obtained liquid for 13 h. wherein TLC is preferably used to detect the reaction; stopping reaction until the raw materials are basically disappeared, adding ethyl acetate to the reaction sample and condensing it at reduced pressure, then dissolving the residue with methanol, adding silica gel and evaporating the resultant liquid to dryness at a reduced pressure and agitating, and eluting with benzene:acetone=4:1 as the eluent to obtain a white powder as compound 1.

Synthesis of LQC-T2 (Compound 2)

Adding the prepared 2-bromomethyl-3,5,6-trimethylpyrazine and protocatechuic acid at a ratio of (3.1-3):1 into a reaction solvent and then adding alkali, agitating at 80-90□ for 1-3 h; stopping reaction until the raw materials are basically disappeared, post-treating and then separating the resultant mixture to obtain compound 2;

Preferably, adding the prepared 2-bromomethyl-3,5,6-trimethylpyrazine and protocatechuic acid at a ratio of 3.1:1 into DMF, and then adding kalium carbonate, agitating at 90° C. for 3 h, wherein TLC is preferably used to detect the reaction; stopping the reaction until the raw materials are basically disappeared, adding ethyl acetate to the reaction liquid and condensing it, then dissolving the residue with a solvent, adding silica gel and evaporating the resultant sample to dryness at a reduced pressure and agitating, and eluting with benzene: acetone=(3-6):1 as the eluent to obtain a powder as compound 2;

More preferably, adding the prepared 2-bromomethyl-3,5,6-trimethylpyrazine and protocatechuic acid at a ratio of 3:1 into DMF, and the adding kalium carbonate, agitating at 80° C. for 2 h under $N_2$ protection, wherein TLC is preferably used to detect the reaction, stopping reaction until the raw materials are basically disappeared, next, adding ethyl acetate to the reaction liquid and condense it at reduced pressure, then dissolving the residue with acetone, adding silica gel and evaporating the resultant sample to dryness at a reduced pressure and agitating, and eluting with benzine:acetone=6:1 as the eluent to obtain a white powder as compound 2.

Synthesis of LQC-T3 (Compound 3)

Adding the prepared 2-bromomethyl-3,5,6-trimethylpyrazine and vanillic acid at a ratio of 1:(1-1.5) into a reaction solvent and then adding alkali, refluxing and agitating the reaction liquid for 4-6 h, stopping reaction until the raw materials are basically disappeared, post-treating and then separating the mixture to obtain compound 3;

Preferably, adding the prepared 2-bromomethyl-3,5,6-trimethylpyrazine and vanillic acid at a ratio of 1:1.3 into acetone, and then adding kalium carbonate, refluxing and agitating the reaction liquid for 6 h, wherein TLC is preferably used to detect the reaction, stopping reaction until the raw materials are basically disappeared, kalium carbonate being removed by filtration and the filtrate being condensed to contain a small amount of solvent, adding silica gel thereinto and evaporating the resultant sample to dryness at a reduced pressure and agitating, and eluting with benzene: ethyl acetate=(7-9): 1 as the eluent to obtain a colorless crystal as compound 3;

More preferably, adding the prepared 2-bromomethyl-3,5,6-trimethylpyrazine and vanillic acid at a ratio of 1:1.6 into acetone, and then adding kalium carbonate, refluxing and agitating the reaction liquid for 5 h, wherein TLC is preferably used to detect the reaction, stopping reaction until the raw materials are basically disappeared, kalium carbonate being removed by filtration and the filtrate being condensed to contain a small amount of acetone, adding silica gel thereinto and evaporating the resultant sample to dryness at a reduced pressure and agitating, and eluting with benzene: ethyl acetate=7.5:1 as the eluent to obtain a colorless crystal as compound 3.

Synthesis of LQC-T4 (Compound 4)

Adding the prepared 2-bromomethyl-3,5,6-trimethylpyrazine and vanillic acid at a ratio of (2-2.1):1 into a reaction solvent and then adding alkali, refuxing and agitating the reaction liquid for 4-6 h, stopping reaction until the raw materials are basically disappeared, post-treating and then separating the resultant mixture to obtain compound 4;

Preferably, adding the prepared 2-bromomethyl-3,5,6-trimethylpyrazine and vanillic acid at a ratio of 2.1:1 into DMF, and then adding kalium carbonate, refuxing and agitating the reaction liquid for 6 h, wherein TLC is preferably used to detect the reaction, stopping reaction until the raw materials are basically disappeared, kalium carbonate being removed by filtration, and then adding a solution into the reaction liquid to dilute, next, extracting with ethyl acetate and combining the extract and evaporating to dryness, the residue being re-dissolved with a small amount of solvent and adding silica gel and evaporating the resultant sample to dryness at a reduced pressure and agitating, and then eluting with benzene: ethyl acetate=(5-8):1 as the eluent to obtain a white powder as compound 4;

More preferably, adding the prepared 2-bromomethyl-3,5,6-trimethylpyrazine and vanillic acid at a ratio of 2:1 into DMF, and then adding kalium carbonate, refuxing and agitating the reaction liquid for 5 h, wherein TLC is preferably used to detect the reaction, stopping reatction until the raw materials are basically disappeared, kalium carbonate being removed by filtration, and then adding saturated sodium bicarbonate aqueous solution to dilute, extracting with ethyl acetate and combining the extract and evaporating to dryness, next, the residue being re-dissolved with a small amount of acetone, adding silica gel and evaporating the resultant sample to dryness at a reduced pressure and agitating, then eluting with benzene:ethyl acetate=6:1 as the eluent to obtain a white powder as compound 4.

Synthesis of LQC-T5 (Compound 5)

Adding the prepared 2-bromomethyl-3,5,6-trimethylpyrazine and protocatechualdehyde at a ratio of (2-3):1 into a reaction solvent and then adding alkali, agitating the reaction liquid at 80-90° C. for 1-3 h, stopping reaction until the raw materials are basically disappeared, post-treating and then separating the resultant mixture to obtain compound 5.

Preferably, adding the prepared 2-bromomethyl-3,5,6-trimethylpyrazine and protocatechualdehyde at a ratio of 2.5:1 into DMF, and then adding kalium carbonate, agitating the reaction liquid at 85° C. for 3 h, wherein TLC is preferably used to detect the reaction, stopping reaction until the raw materials are basically disappeared, kalium carbonate being removed by filtration, and then adding a solution into the reaction liquid to dilute, extracting with ethyl acetate and combining the extract and evaporating the resultant liquid to dryness, the residue being re-dissolved with a small amount of solvent, adding silica gel and evaporate the resultant sample to dryness at a reduced pressure and agitating, and then eluting with benzene: ethyl acetate=(5-8):1 as the eluent to obtain a white powder as compound 5.

More preferably, adding the prepared 2-bromomethyl-3,5,6-trimethylpyrazine and protocatechualdehyde at a ratio of 2.8:1 into DMF, and then adding kalium carbonate, agitating the reaction liquid at 85° C. for 2 h with $N_2$ protection, wherein TLC is preferably used to detect the reaction, stopping reaction until the raw materials are basically disappeared, kalium carbonate being removed by filtration, and then adding saturated sodium bicarbonate aqueous solution to dilute, extracting with ethyl acetate and combining the extract and evaporating to dryness, next, the residue being re-dissolved with a small amount of acetone, adding silica gel and evaporating the resultant sample to dryness at a reduced pressure and agitating, and then eluting with benzene:ethyl acetate=7:1 as the eluent to obtain a white powder as compound 5.

Synthesis of LQC-T6 (Compound 6)

Adding the prepared 2-bromomethyl-3,5,6-trimethylpyrazine and caffeic acid at a ratio of (3-4):1 into a reaction solvent and then adding alkali, agitating the reaction liquid at 80-90° C. for 1-3 h, stopping reaction until the raw materials are basically disappeared, post-treating and then separating the resultant mixture to obtain compound 6.

Preferably, adding the prepared 2-bromomethyl-3,5,6-trimethylpyrazine and caffeic acid at a ratio of 3.5:1 into DMF, and then adding kalium carbonate, agitating the reaction liquid at 85° C. for 3 h, wherein TLC is preferably used to detect the reaction, stopping reaction until the raw materials are basically disappeared, kalium carbonate being removed by filtration, and then adding a solution into the reaction liquid to dilute, extracting with ethyl acetate and combining the extract and evaporating to dryness, next, the residue being re-dissolved with a small amount of solvent, adding silica gel and evaporating the resultant sample to dryness at a reduced pressure and agitating, and then eluting with benzene: acetone=6-9:1 as the eluent to obtain a white powder as compound 6.

More preferably, adding the prepared 2-bromomethyl-3,5,6-trimethylpyrazine and caffeic acid at a ratio of 3.8:1 into DMF, and then adding kalium carbonate, agitating the reaction liquid at 85° C. for 2 h with $N_2$ protection, wherein TLC being preferably used to detect the reaction, stopping reaction until the raw materials are basically disappeared, kalium carbonate being removed by filtration, and then adding saturated sodium bicarbonate aqueous solution to dilute, extracting with ethyl acetate and combining the extract and evaporating to dryness. next, the residue being re-dissolved with a small amount of acetone, adding silica gel and evaporating the resultant sample to dryness at a reduced pressure and agitating, and then eluting with benzene: acetone=8:1 as the eluent to obtain a white powder as compound 6.

DETAILED DESCRIPTION OF THE PREFERRED EMBODIMENT

The examples of the compounds of the present invention are provided as below; however, these examples should be considered limitations of the present invention.

Example 1

The Preparation of 2-Bromomethyl-3,5,6-Trimethylpyrazine Intermediate

Dehydrated tetramethylpyrazine 10 g was dissolved into $CCl_4$ 60 ml and then NBS 9.17 g was added at a molar ratio of tetramethylpyrazine to NBS=1:0.7 (a minute amount of benzoylperoxide can be added as radical initiator). Reaction was carried out under reflux under the illumination of an incandescent lamp for 10-12 h. The reaction sample was cooled and condensed, and the excess tetramethylpyrazine was sucked away at reduced pressure in 60-70° C. water bath. The residue was kept in a fridge for standing and a pale red half-oily substance 7.75 g was obtained with a yield of 70%.

Example 2

Synthesis of LQC-T1 (Compound 1)

2-bromomethyl-3,5,6-trimethylpyrazine 3.26 mmol prepared in example 1 and protocatechuic acid 3.40 mmol were put into a 50 ml round bottom flask and then xylene 30 ml was added. Triethylamine 3 mmol was added after the mixture was dissolved. The reaction liquid was heated and refluxed for 12 h. The reaction was stopped when the raw materials were basically disappeared by the detection of TLC. Next, ethyl acetate 30 ml was added into the reaction liquid followed by being condensed at reduced pressure. The residue was dissolved by methanol 4 ml, silica gel 2.0 g was added thereinto, and the resultant sample was evaporated to dryness at a reduced pressure and was agitated. The obtained mixture was eluted with benzene: acetone=5:1 as the eluent to obtain a white powder 0.45 g. The yield was 48.0%, and the melting point was 219.2-220.1° C., FAB-MS m/z 289 [M+H]$^+$; the hydrogen spectrum and carbon spectrum NMR data of compound 1 were as follows:

$^1$HNMR (500 MH$_z$, DMSO-d$^6$): 7.353-6.802 (m, 3H, Ar—H), 5.323 (s, 2H, O—CH$_2$), 2.503 (s, 3H, 6-CH$_3$), 2.455 (s, 3H, 5-CH$_3$), 2.431 (s, 3H, 3-CH$_3$), 9.855 (s, H, 4-OH), 9.421 (s, H, 3-OH);

$^{13}$CNMR (125 MHz, DMSO-d$^6$): 166.7 (—COO), 122.5 (Ar—C-1), 116.7 (Ar—C-2), 145.4 (Ar—C-3), 151.4 (Ar—C-4), 115.9 (Ar—C-5), 120.6 (Ar—C-6), 66.3 (—CH$_2$—O), δC of the pyrazine ring: 151.1 (C-2), 145.6 (C-3), 148.9 (C-5), 149.2 (C-6), 21.7 (6-CH$_3$), 21.5 (5-CH$_3$), 20.6 (3-CH$_3$).

Example 3

Synthesis of LQC-T2 (Compound 2)

2-bromomethyl-3,5,6-trimethylpyrazine 4.6 mmol prepared in Example 1 and protocatechuic acid 1.5 mmol were put into a 25 ml round bottom flask and DMF 14 ml was added. Kalium carbonate 10 mmol was added after the mixture was dissolved. The resultant mixture was agitated at 85° C. for 1.5 h with N$_2$ protection. The reaction was stopped when the raw materials were basically disappeared by the detection of TLC. The kalium carbonate was removed by filtration. Then the reaction liquid was diluted by adding saturated sodium bicarbonate aqueous solution and extracted with ethyl acetate for 3 times. The extract was combined and evaporated to dryness. The residue was re-dissolved with a small amount of acetone, silica gel 3.0 g was added and the resultant sample was evaporated to dryness at a reduced pressure and was agitated. The obtained mixture was eluted with benzine: acetone=6:1 as the eluent to obtain a white powder 0.36 g. The yield was 43.1%; the melting point was 202.2203.0° C., FAB-MS m/z 557 [M+H]$^+$.

The hydrogen spectrum and carbon spectrum NMR data of compound 2 were as follows:

$^1$HNMR (500 MHz, CDCl$_3$): 7.695 (d, 1H, J=2 Hz, Ar—H-2), 7.095 (d, 1H, J=8.5 Hz, Ar—H-5), 7.760 (d, 1H, J=2, J=8.5 Hz, Ar—H-6), 5.427 (s, 2H, 1-ester-CH$_2$), 5.235 (s, 2H, 3-ether-CH$_2$), 5.173 (s, 2H, 4-CH$_2$), 2.4702.602 (m, 27H, pyrazine ring-CH$_3$);

$^{13}$CNMR (125 MHz, CDCl$_3$): 165.8 (—COO), 124.5 (Ar—C-1), 115.4 (Ar—C-2), 151.3 (Ar—C-3), 152.8 (Ar—C-4), 113.1 (Ar—C-5), 122.8 (Ar—C-6), 65.8 (—CH$_2$-ester), 70.8 (—CH$_2$—O-3), 71.1 (—CH$_2$—O-4), ester-δC of pyrazine ring: 150.1 (C-2), 145.1 (C-3), 148.1 (C-5), 149.0 (C-6), 21.6 (6-CH$_3$), 21.3 (5-CH$_3$), 20.5 (3-CH$_3$), 3-ether-δC of pyrazine ring: 151.1 (C-2), 145.1 (C-3), 148.6 (C-5), 149.3 (C-6), 21.6 (6-CH$_3$), 21.3 (5-CH$_3$), 20.6 (3-CH$_3$), 4-ether-δC of pyrazine ring: 151.3 (C-2), 145.4 (C-3), 148.6 (C-5), 150.0 (C-6), 21.7 (6-CH$_3$), 21.5 (5-CH$_3$), 20.6 (3-CH$_3$).

Example 4

Synthesis of LQC-T3 (Compound 3)

2-bromomethyl-3,5,6-trimethylpyrazine 2.60 mmol prepared in Example 1 and vanillic acid 3.26 mmol were put into a 25 ml three-necked flask and 18 ml acetone was added. Kalium carbonate 5 mmol was added after the mixture was dissolved. The reaction liquid was heated and refluxed for 5 h. The reaction was stopped when the raw materials were basically disappeared by TLC detection. The kalium carbonate was removed by filtration. The filtrate was condensed to contain a small amount of acetone, silica gel 2.0 g was added to evaporate to dryness at a reduced pressure and was agitated. The resultant mixture was eluted with benzene: ethyl acetate=7.5:1 as the eluent to obtain a colorless crystal 0.32 g. The yield was 40.7% and the melting point was 151.4-152.3° C. FAB-MS m/z 303 [M+H]$^+$. The hydrogen spectrum and carbon spectrum NMR data of compound 3 were as follows:

$^1$HNMR (500 MHz, CDCl$_3$): 7.6336.897 (m, 3H, Ar—H), 5.407 (s, 2H, O—CH$_2$), 2.581 (s, 3H, 6-CH$_3$), 2.524 (s, 3H, 5-CH$_3$), 2.510 (s, 3H, 3-CH$_3$), 6.196 (s, H, 4-OH), 3.907 (s, 3H, —OCH$_3$);

$^{13}$CNMR (125 MHz, CDCl$_3$): 165.9 (—COOH), 124.4 (Ar—C-1), 111.8 (Ar—C-2), 151.3 (Ar—C-3), 150.3 (Ar—C-4), 114.1 (Ar—C-5), 121.7 (Ar—C-6), 65.7 (—CH$_2$—O), 56.1 (O—CH$_3$), δC of pyrazine ring: 149.3 (C-2), 145.1 (C-3), 146.2 (C-5), 149.0 (C-6), 21.6 (6-CH$_3$), 21.4 (5-CH$_3$), 20.6 (3-CH$_3$).

Example 5

Synthesis of LQC-T4 (Compound 4)

2-bromomethyl-3,5,6-trimethylpyrazine 6.52 mmol prepared in Example 1 and vanillic acid 3.26 mmol were put into a 25 ml three-necked flask and 18 ml DMF was added. Kalium carbonate 8 mmol was added after the mixture was dissolved, the resultant mixture was heated and refluxed for 4 h. The reaction was stopped when the raw materials were basically disappeared by TLC detection. The kalium carbonate was removed by filtration. Then the reaction liquid was diluted by adding saturated sodium bicarbonate aqueous solution and extracted with ethyl acetate for 3 times. The extract was combined and evaporated to dryness. The residue was re-dissolved with a small amount of acetone, silica gel 4 g was added and the resultant sample was evaporated to dryness at reduced pressure and was agitated. The obtained mixture was eluted with benzene:ethyl acetate=6:1 as the eluent to obtain a white powder 0.92 g. The yield was 60.0% and the melting point was 78.5-79.4° C. FAB-MS m/z 437 [M+H]$^+$.

The hydrogen spectrum and carbon spectrum NMR data of compound 4 were as follows:

$^1$HNMR (500 MHz, CDCl$_3$): 7.6357.036 (m, 3H, Ar—H), 5.406 (s, 2H, COO—CH$_2$), 5.248 (s, 2H, Ar—O—CH$_2$), 2.5962.492 (s, 18H, pyrazine ring-CH$_3$), 3.706 (s, 3H, OCH$_3$);

$^{13}$CNMR (125 MHz, CDCl$_3$): 165.9 (—COOH), 123.5 (Ar—C-1), 112.6 (Ar—C-2), 151.4 (Ar—C-3), 152.1 (Ar—C-4), 112.7 (Ar—C-5), 122.8 (Ar—C-6), 70.7 (—CH$_2$—O ether), 65.7 (—CH$_2$—O ester), 56.0 (O—CH$_3$), δC of pyrazine ring: ester structure part 151.3 (C-2), 145.1 (C-3), 149.0 (C-5), 149.3 (C-6), 21.6 (6-CH$_3$), 21.4 (5-CH$_3$), 20.6 (3-CH$_3$). Ether structure part 150.1 (C-2), 145.1 (C-3), 148.6 (C-5), 149.2 (C-6), 21.6 (6-CH$_3$), 21.4 (5-CH$_3$), 20.6 (3-CH$_3$).

Example 6

Synthesis of LQC-T5 (Compound 5)

2-bromomethyl-3,5,6-trimethylpyrazine 4.0 mmol prepared in Example 1 and protocatechualdehyde 1.4 mmol were put into a 25 ml round bottom flask and 14 ml DMF was added. Kalium carbonate 10 mmol was added after the mixture was dissolved. The resultant mixture was agitated at 85☐ for 2 h with N$_2$ protection. The reaction was stopped when the raw materials were basically disappeared by TLC detection. The kalium carbonate was removed by filtration. Then the reaction liquid was diluted by adding saturated sodium bicarbonate aqueous solution and extracted with ethyl acetate for 2 times. The extract was combined and evaporated to dryness. The residue was re-dissolved with a small amount of acetone, silica gel 3 g was added and the resultant sample was evaporated to dryness at reduced pressure and was agitated. The obtained mixture was eluted with benzene: acetone=7:1 as the eluent to obtain a white powder 0.23 g. The yield was 40.3% and the melting point was 138.4-139.7° C. FAB-MS m/z 407 [M+H]$^+$.

The hydrogen spectrum and carbon spectrum NMR data of compound 5 are as follows:

$^1$HNMR (500 MHz, CDCl$_3$): 9.861 (s, 1H, —CHO) 7.640 (s, 1H, Ar—H-2), 7.213 (d, 1H, J=8.5 Hz, Ar—H-5), 7.482 (d, 1H, J=1.5 Hz, J=8.5 Hz, Ar—H-6), 5.282 (s, 2H, 3-ether-CH$_2$), 5.239 (s, 2H, 4-ether-CH$_2$), pyrazine ring 2.573 (brs, 6H, 6-CH$_3$), 2.536 (brs, 6H, 5-CH$_3$), 2.525 (brs, 6H, 3-CH$_3$);

$^{13}$CNMR (125 MHz, CDCl$_3$): 190.7 (—CO—), 130.5 (Ar—C-1), 113.1 (Ar—C-2), 149.0 (Ar—C-3), 153.9 (Ar—C-4), 112.6 (Ar—C-5), 126.6 (Ar—C-6), 70.8 (—CH$_2$—O-3), 70.9 (—CH$_2$—O-4), 3-ether-δC of pyrazine ring: 151.1 (C-2), 145.0 (C-3), 148.7 (C-5), 149.8 (C-6), 21.5 (6-CH$_3$), 21.3 (5-CH$_3$), 20.4 (3-CH$_3$), 4-ether-δC of pyrazine ring: 151.4 (C-2), 145.4 (C-3), 148.9 (C-5), 150.1 (C-6), 21.6 (6-CH$_3$), 21.4 (5-CH$_3$), 20.5 (3-CH$_3$).

Example 7

Synthesis of LQC-T6 (Compound 6)

2-bromomethyl-3,5,6-trimethylpyrazine 8.0 mmol prepared in Example 1 and caffeic acid 2.3 mmol were put into a 25 ml round bottom flask and 17 ml DMF was added. Kalium carbonate 13 mmol was added after the mixture was dissolved. The obtained mixture was agitated at 85° C. for 2.5 h with N$_2$ protection. The reaction was stopped when the raw materials were basically disappeared by TLC detection. The kalium carbonate was removed by filtration. Then the reaction liquid was diluted by adding saturated sodium bicarbonate aqueous solution and extracted with ethyl acetate for 2 times. The extract was combined and evaporated to dryness. The residue was re-dissolved with a small amount of acetone, silica gel 3 g was added and the resultant sample was evaporated to dryness at reduced pressure and was agitated. The obtained mixture was eluted with benzene: acetone=8:1 as the eluent to obtain a white powder 0.58 g. The yield was 43.2% and the melting point was 151.6-152.7° C. FAB-MS m/z 583 [M+H]$^+$. The hydrogen spectrum and carbon spectrum NMR data of compound 6 were as follows:

$^1$HNMR (500 MHz, CDCl$_3$): 7.350 (s, 1H, Ar—H-2), 7.061 (m, 2H, Ar—H-5,6), 6.366 (d, 1H, J=16 Hz, C=CH—COO), 7.635 (d, 1H, J=16 Hz, Ar—CH=C), 5.213 (brs, 4H, 3,4-ether-CH$_2$), 5.341 (s, 2H, ester-CH$_2$), 2.5042.603 (m, 27H, pyrazine ring —CH$_3$);

$^{13}$CNMR (125 MHz, CDCl$_3$): 166.7 (—COO), 128.0 (Ar—C-1), 115.5 (Ar—C-2), 151.1 (Ar—C-3), 151.2 (Ar—C-4), 113.2 (Ar—C-5), 123.3 (Ar—C-6), 65.1 (—CH$_2$-ester), 70.9 (—CH$_2$—O-3), 71.0 (—CH$_2$—O-4), 113.9 (C=CH—COO), 145.2 (Ar—CH=C), ester-δC of pyrazine ring: 150.0 (C-2), 145.2 (C-3), 148.6 (C-5), 149.1 (C-6), 21.6 (6-CH$_3$), 21.4 (5-CH$_3$), 20.4 (3-CH$_3$), 3-ether-δC of pyrazine ring: 150.0 (C-2), 145.4 (C-3), 148.6 (C-5), 149.2 (C-6), 21.6 (6-CH$_3$), 21.4 (5-CH$_3$), 20.5 (3-CH$_3$), 4-ether-δC of pyrazine ring: 151.2 (C-2), 145.6 (C-3), 148.6 (C-5), 150.0 (C-6), 21.6 (6-CH$_3$), 21.5 (5-CH$_3$), 20.5 (3-CH$_3$).

The following experiment examples and examples further prove the present invention but can't be considered as limitations to the present invention.

Effect Example 1

Observing the Effect of LQC-T on the CAM Angiogenesis Using CAM Method

1. Material 1.1 Animal

Embryonated chicken eggs of Lohmann of German, egg weight 50-60 g (embryo experiment center of Chinese Agriculture University)

1.2 Experimental Medicine

LQC-T (1-6) (prepared by the methods of examples 2-7), wherein the purity was ≥98%, determined by high performance liquid chromatography (HPLC), meeting the requirements of the experiment. The powder was carefully sealed and preserved at 4° C.

2. Method 2.1 Preparation Method of the Sample to be Tested

Aseptic gelatin sponge, which was made into a wafer having a diameter of 5 mm by a hole-puncher in advance, was used as sample carrier. The prepared LQC-T series compounds were added according to 20 μg/chicken embryo in an aseptic environment. The 0.9% physiological saline was used in a blank group. The samples were air-dried in an aseptic environment.

2.2 Egg Embryo Incubation and the Removing Method of Egg Embryo Air Sac

A hatching egg after disinfection was put into a 37° C. incubation box with air sac upward until the seventh day of incubation. The egg embryo was disinfected using alcohol at a super clean bench, and then a small hole was drilled at the top of the egg embryo using a dental drill, and the nearby egg shell and shell membrane were removed carefully to form the opening with the size of about 1.2 cm×1.2 cm. After spotting the location for applying the sample, the air sac was broken with injection needle at the interface between air sac and the yolk and then 1-2 drops of aseptic physiological saline was injected so that the air sac membrane was separated from CAM membrane. Then the upper air sac membrane was slightly removed with a nipper to expose the lower CAM membrane.

2.3 Sample Applying Method

The medicine-containing carrier was softly put by a nipper at the locations of CAM and yolk cyst membrane with fewer vessels, the opening was then sealed with aseptic transparent tape and incubation was continued for another 72 h.

2.4 Vessel Determination

After the incubation, the transparent tape blocking the chicken embryo air sac was removed with a nipper. The liquid of equal-volumetrically mixed methanol/acetone 1-2 ml was added and fixed at room temperature for 10 min. The CAM membrane was carefully removed and put it onto a slide. Then it was observed and a photograph was taken. The effect of the compounds on angiogenesis was evaluated by the count analytic method using the numbers of great vessels, medium vessels and small vessels arranged radially around by the carrier.

2.5 Statistical Treatment

All the data were statistically analyzed using SPSS11.0 software pack. The difference between the administration group and the blank group was given through one-way variance analysis. $P<0.05$ had statistical significance.

3. Result

Repectively compared with the blank group about the amount of the small vessels, all the LQC-T administration groups had a vessel growth promoting effect, wherein LQC-T2 and LQC-T4 had significant promoting effect according to table 1, which showed that LQC-Y all had promoting effect on the growth of the new vessels.

TABLE 1 effect of LQC-T on small vessel angiogenesis of CAM model ($\overline{X} \pm S$)

| Medicine No. | Blank group ($\overline{X} \pm S$) | Medicine group ($\overline{X} \pm S$) | Dosage (μg/chicken embryo) | Number of chicken embryo |
|---|---|---|---|---|
| LQC-T1 | 8.67 ± 1.03 | 12.7 ± 2.73 | 20 | 20 |
| LQC-T2 | 8.67 ± 1.03 | 14.17 ± 1.47** | 20 | 20 |
| LQC-T3 | 8.67 ± 1.03 | 10.4 ± 2.16 | 20 | 20 |
| LQC-T4 | 8.67 ± 1.03 | 14.4 ± 2.16** | 20 | 20 |
| LQC-T5 | 8.67 ± 1.03 | 14.17 ± 5.19 | 20 | 20 |
| LQC-T6 | 8.67 ± 1.03 | 8.83 ± 3.71 | 20 | 20 |

Note:
compared with the blank group,
*P < 0.05,
**P < 0.01

4. Conclusion

LQC-T (1-6) all had a certain effect on promoting the growth of the vessels wherein LQC-T2 and LQC-T4 had magnificent effect on promoting the growth of new vessels.

Effect Example 2

Observing the Effect of LQC-T4 on the Proliferation of Primary Neuronal Cells by MTT 1. Material
1.1 Experimental Animal SD pregnant rats: pregnant for 16-18 d, certificate number: SCXK (Jing) 2006-0009, provided by BeiJing Vital River Laboratories.

1.2 Experimental Medicine

LQC-T4 (prepared by the method of example 5), the purity was ≥98%, determined by high performance liquid chromatography (HPLC), which met the requirement of the experiment. The powder was carefully sealed and preserved at 4° C. The prepared LQC-T4 was dissolved using dimethyl sulfoxide and made into 1 ml/mg storing liquid for use.

2 Method
2.1 The Culture of the Rat Primary Cortical Neurons

Referring to the document [HongQingtao, TangYipeng, Neurons of cerebral cortex of newborn rats in in vitro primary culture, Chinese Journal of Neuroanatomy, 1994, 10(3):259-262], the pregnant 16-18 d SD rat was executed by dislocation. The fetal rat was taken out in an aseptic environment, the meninges and blood steak were stripped, the cortex was separated and cut into 1 $mm^3$ tissue block (all carried out on ice). The tissue block was digested at 37□ with 0.1% pancreatic enzyme-0.02% EDTA for 20 min. Digesting was stopped using DMEM containing fetal calf serum and the number of the cells was adjusted to 5×$10^5$ cells $ml^{-1}$. The resultant cells were inoculated into a 96 well plate treated by 0.001% polylysine and the plate was put in a 37° C. 5% $CO_2$ incubation box to be cultured. The cultivation liquid was changed (totally) after 48 h and add adenine arabinoside was added (final concentration is 5 μM) to inhibit the excessive proliferation of non-neurons. The cultivation liquid was changed after 48 h with fresh cultivation liquid and culture was continued. And the cultivation liquid was changed every 3 days afterward.

2.2 The Effect of LQC-T4 on the Normal Neurons

The cultivation liquid was sucked away on the eighth day of neuron culture. DMEM culture-medium containing 0.15% DMSO was added to the blank group, while 60 μM, 30 μM, 15 μM LQC-T4, 60 μM tetramethylpyrazine and 60 μM vanillic acid were respectively added to the administration group. Ten parallel wells were set as a group. And they were put into a 37° C., 5% $CO_2$ incubation box to continue culturing for 24 h.

2.3 Morphology Observation:

The growth and the morphologic change of the neurons were observed with inverted phase contrast microscope.

2.4 Determination of the Cell Activity Using MTT Method:

5 mg/ml MTT 20 μl was added to each well at the time of 4 h before the experiment ended and the cultivation liquid was sucked away. DMSO 200 μl was added to each well. When the purple particles were completely dissolved, the enzyme-linked immune assay was used to measure the optical density at 540 nm.

2.5 Statistical Treatment:

The SAS 8.2 statistical software was used to carry out the one-way ANOVA variance analysis and the difference among the groups were compared by t-test.

3 Result
3.1 Morphology Observation:

when observing the primary neuronal cells cultured in vitro under phase contrast microscope, the normal group neurons had clear spatial effect and appeared as a cone shape with multipoles, and their protrusions were clear. The LQC-T4 group cells were more prosperous in growth and their protrusions formed a network.

3.2 Measuring the Cell Activity Using MTT Method

Every administration group showed a promoting effect on the growth of normal neurons after 24 h after the administration, however no magnificent difference was observed (P>0.05). And the promoting effect of the LQC-T4 administration group was greater than that of the tetramethylpyrazine group and the vanillic acid group. The results were shown in table 2.

TABLE 2 effect of LQC-T4 on the proliferation of the primary neuronal cells

| group | N | dosage (μM) | MTT(A540), 24 h after the administration |
|---|---|---|---|
| control | 6 | — | 0.7567 ± 0.1109 |
| LQC-T4 (large dosage) | 6 | 60 | 0.8106 ± 0.2415 |
| LQC-T4 (middle dosage) | 6 | 30 | 0.9114 ± 0.1599 |
| LQC-T4 (small dosage) | 6 | 15 | 0.9175 ± 0.2300 |
| TMP | 6 | 60 | 0.8710 ± 0.1350 |
| Vanillic acid | 6 | 60 | 0.8820 ± 0.1469 |

4. Conclusion

LQC-T4 had an obvious proliferation effect on the primary neuronal cells, and the effect of which showed a negative correlation with the medicine concentration, wherein the proliferation effect of the LQC-T4 was the best at lower concentration.

Effect Example 3

Effect of LQC-T4 on Buccal Respiration Duration of Mice after Head Cutting

1. Materials
1.1 Materials
1.1.1 Experimental Animals

ICR mice, half female and half male, weighing 19-21 g, certificate No.: SCXK (Jing) 2006-0009, provided by BeiJing Vital River Laboratories.

1.1.2 Medicines

LQC-T4, tetramethylpyrazine (TMP), vanillic acid, Nimodipine (ShanDong XinHua Pharmaceutical CO., Ltd, batch No.: 0908164)

2.2 Method 2.2.1 Grouping and Administration 160 male ICR mice were divided into 8 groups randomly by weight, each of which contained 20 mice, wherein 0.5% CMC-NA (0.2 ml·10 g$^{-1}$) was administrated intragastrically to the blank control group; 6.7 mg·kg$^{-1}$ Nimodipine (0.2 ml·10 g$^{-1}$) was administrated intragastrically to the positive control group; 100 mg·kg$^{-1}$ TMP (0.2 ml·10 g$^{-1}$) was administrated intragastrically to the TMP group, three different dosage of 200 mg·kg$^{-1}$, 100 mg·kg$^{-1}$, 50 mg·kg$^{-1}$ were administrated intragastrically to the LQC-T4 (0.2 ml·10 g$^{-1}$) group relatively, and 125 mg·kg$^{-1}$ TMP+80 mg·kg$^{-1}$ vanillitc acid (0.2 ml·10 g$^{-1}$) was administrated intragastrically respectively. The medicines were continuously administrated once a day for 10 days.

2.2.2 Modeling Method

The literature was referred to: [LiuZhenquan, SunHui, Xuqiuping, etc., Experimental Study on the Brain-Protective Effect of the Effective Fraction of Naoxin Formula in the Mouse Model of with Load-Bearing Swimming in Cold Water, Journal of Beijing University of Traditional Chinese Medicine [J], 2004, 27(4): 54-56] and the method recorded therein was improved. The head was rapidly cut with a scissor at post mortem when the mouse swam in 4° C. icy water for 3 min after the final administration. After head being cut, the buccal respiration duration of mouse was recorded.

2.5 Statistical Treatment

The SAS 8.2 statistical software was used to carry out the one-way ANOVA variance analysis and the difference among the groups were compared by t-test.

2.3 Result

Compared with the blank control group, the Nimodipine group, the TMP+vanillitc acid mechanically mixed group and the LQC-T4 group can all prolong the buccal respiration duration of mice after head being cut to different extents. The results were shown in table 3.

TABLE 3 effect of LQC-T4 on buccal respiration duration of mice after head cutting

| group | Dosage (mg/kg) | n | respiration duration (s) |
|---|---|---|---|
| Control group (0.5% CMC-Na) | — | 19 | 32.45 ± 5.49 |
| Nimodipine | 6.7 | 18 | 37.23 ± 5.37* |
| LQC-T4 (large dosage) | 200 | 20 | 35.91 ± 4.25* |
| LQC-T4 (middle dosage) | 100 | 17 | 36.07 ± 3.15* |
| LQC-T4 (small dosage) | 50 | 19 | 36.78 ± 5.40* |
| TMP | 125 | 18 | 37.26 ± 5.99* |
| vanillic acid | 80 | 19 | 35.73 ± 5.66 |
| TMP + vanillic acid | 125 + 80 | 20 | 38.17 ± 4.65** |

Note:
compared with the control group,
*P < 0.05,
**P < 0.01

3. Conclusion

The three dosage groups of large dosage, middle dosage and small dosage of LQC-T4 all can prolong the buccal respiration duration of mice in the 4° C. icy water swimming model after head being cut.

Effect Example 4

Effect of LQC-T4 on the Recovering Nerve Function after Cerebral Ischemia

1. Materials 1.1 Experimental Animals 140 healthy SD male rats, weighing 280-300 g, provided by Beijing Vital River Laboratories, certificate No.: SCXK (Jing) 2002-2003.

1.2 Experimental Instrument

Nylon fishing wire, diameter 0.25 mm, German; YLS-13A, grip strength meter for mice and rats, Shandong Science Technology Instrument Station.

1.3 Experimental Medicine

Tetramethylpyrazine (TMP), vanillic acid, LQC-T4 (self made), the purity ≥98%, determined using high performance liquid chromatography (HPLC), which met the requirement of experiment, the powder being carefully sealed and preserved at 4° C., and imodipine (ShanDong XinHua Pharmaceutical CO., Ltd, batch No.: 0908164).

2 Method 2.1 The Establishing of the Animal Model

The method of [Koizumi J, Yoshida Y, Nakazawa T, Ooneda G. Experimental studies of ischemia brain edema, I: A new experimental model of cerebral embolism in rats in which recirculation can be introduced in the ischemic area[J]. Jpn J Stroke, 1986, 8:1-8] was referred to in order to establish the MCAO model. After the rats were anesthetized and the skin thereof was disinfected by ethanol. By cutting right in the middle of the neck, the right common carotid artery, internal carotid artery and external carotid artery were separated and the common carotid artery and external carotid artery were ligated. The internal carotid artery was clamped with a bull-dog clamp. A cut was made at the crotch of the external carotid artery and the internal carotid artery followed by releasing the bulldog clamp. The nylon wire was inserted into the cut with the deep of about a little longer than 18 mm to achieve the cerebral ischemia caused by cerebral artery occlusion. Next, the external carotid artery was ligated and the nylon wire was fixed. In sham operation group, the right common carotid artery, the external carotid artery and the internal carotid artery were only exposed and separated. The rats were routinely raised in different cages. 0.5 ml penicillin was continuously injected into every mouse for three days after the surgery.

2.2 The Judgment on Whether the Model was Successful and the Evaluating Method of the MCAO Rats Neurological Symptoms The evaluating standard of the neurological symptoms of MCAO rats were carried out according to the Zea Longa 5 grades evaluating method, that is, the rats were evaluated when they were conscious after 6 h after the surgery: no apparent neurological symptom, 0 point; not being able to completely stretch the left front claw, 1 point; whirling leftward, 2 point; leaning leftward when walking, 3 point; having an epileptic seizure, losing consciousness and not being able to walk independently, as 4 point. The rats getting 1-3 point were selected for the subsequent experiment. The MCAO rats having the same point were distributed randomly and averagely to each experimental group.

2.3 Administration Method

There were sham operation group, model group, Nimodipine group, LQC-T 4 large dosage group, LQC-T4 small dosage group, TMP group and TMP+Vanillic acid group. 0.5% CMC-Na (1 ml·100 g$^{-1}$) was administratrically to the blank group and model group, two dosage groups of 120 mg·kg$^{-1}$ and 60 mg·kg$^{-1}$ were intragastrically administrated to the LQC-T4(1 ml·100 g$^{-1}$) group, and 74 mg·kg$^{-1}$ TMP+46 mg·kg$^{-1}$ vanillite acid (1 ml·100 g$^{-1}$) were intragastrically administrated, once a day continuously for 10 days.

2.4 Testing Method for Sensory Function of Limb Movement 2.4.1 Beam Walking Test Beam walking test was used to evaluate the motor coordination and the integration defect after the cerebral ischemia damage. The beam was 2.0 cm in width, 120 cm in length and 1 cm in thickness, and was horizontally hung in the air at 80 cm from the ground. There was a dark box attached to one end of the beam and the rats were stimulated by noise to walk through the beam into the dark box. The evaluating standard was as follows: not being able to stay on the beam, 0 point; being able to stay on the beam but unable to move, 1 point; trying to pass but falling from the beam, 2 point; being able to walk on the beam but times on the injured hind limb slipping from the beam for being more 50%, 3 point; the times being more than once but less than 50%, 4 point; only slipping once, 5 point; and passing through successfully, 6 point. The rats were trained before the ischemia for 5 days until all the rats can get 6 point. The third and the seventh days after administration was set as the observation time to carry out the test.

2.4.2 Tactile Stimulus Experiment

Evaluated was the executive function change of side forelimb sense and fine motor movement after the cerebral ischemia. A piece of medical adhesive tape of the same area (0.7×0.7 cm$^2$) was put onto the facies ventralis of the left forelimb wrist of the rats as the tactile stimulus and the latent period of the rats removing the tape was recorded. The rats were trained for 5 days, once a day to enable the rats to remove the tape in 20 seconds. The third and the seventh days after the administration were set as the observation time to carry out the test.

2.4.3 Grip Strength Test of the Forelimb

Evaluated was the change of the grip strength of the forelimb after the cerebral ischemia. A rat was put onto the pulling board making the forepaws thereof grab the cross bar. Then the tester pulled the rat backward to make its body slide backward along the board until the release of the forepaws (during this process it was made sure that the waist of the rat carried no force). The biggest grip strength was read when the forepaws released. Test was carried out twice for every rat and the bigger value was taken. The third and the seventh days after the administration were as the observation time to carry out the test.

2.5 Statistical Treatment

The SPSS 11.0 software pack was used to carry out the statistical analysis of all the data. The comparison of the enumeration data was carried out with X$^2$ test P<0.05 had statistical meaning.

3. Experiment Result 3.1 Effect of LQC-T4 on the Neurological Symptoms of the MCAO Rats Rats of the sham operation group showed no behavior of neurologic impairment while rats of other groups showed symptoms of neurologic impairment to different extents after 3 days of cerebral ischemia. The behaviors included: not being able to completely stretch the left front claw, whirling or leaning leftward when walking, even not being able to walk. And these behaviors were improved after the medicine was administrated continuously for 7 days. For both of the Nimodipine group and the LQC-T4 small dosage group, the neurologic impairment symptoms of the cerebral ischemia of the rats after administrated for 3 day and 7 day were improved. The results were showed in table 4.

TABLE 4 effect of LQC-T4 on neurological symptoms of the MCAO rats

| group | dosage (mg/kg) | n | evaluation (3 d) | n | evaluation (7 d) |
|---|---|---|---|---|---|
| sham operation group | — | 15 | 0 ± 0** | 14 | 0 ± 0** |
| Model group | — | 19 | 1.74 ± 0.73 | 13 | 1.61 ± 0.96 |
| Nimodipine | 30 | 17 | 1.35 ± 0.49* | 16 | 1.11 ± 0.48* |
| LQC-T4 (large dosage) | 120 | 17 | 1.29 ± 0.47 | 15 | 1.60 ± 0.74 |
| LQC-T4 (small dosage) | 60 | 15 | 1.40 ± 0.51* | 12 | 1.26 ± 0.35* |
| TMP | 37 | 14 | 1.36 ± 0.50 | 12 | 1.67 ± 0.78 |
| TMP + vanillic acid | 74 + 46 | 8 | 2.25 ± 0.46 | 5 | 1.80 ± 0.84 |

Note:
compared with the model group,
*P < 0.05,
**P < 0.01

3.2.1 Effect of the LQC-4 on the Beam Walking of the MCAO Rats

After administrated for 3 days, the rats of the sham operation group can pass the beam successfully while the beam walking ability of the model group rats clearly dropped, and for the Nimodipine group, the LQC-T4 group and the TMP group rats, the recovery of the beam walking ability was promoted, different from the model group rats. However, the TMP and vanillic acid mechanically mixed group showed no promoting effect. The rats of each group all showed some improvement in the beam walking ability after being administrated for 7 days, wherein the Nimodipine group and the LQC-T4 small dosage group showed magnificent improvement compared with the model group. The results were shown in table 5.

TABLE 5 effect of LQC-T4 on beam walking of the MCAO rats

| group | dosage (mg/kg) | n | Evaluation (3 d) | n | Evaluation (7 d) |
|---|---|---|---|---|---|
| sham operation group | — | 15 | 6 ± 0** | 14 | 6 ± 0** |
| Model group | — | 19 | 1.47 ± 0.84 | 13 | 1.92 ± 2.02 |
| Nimodipine group | 30 | 17 | 2.71 ± 1.49** | 16 | 3.50 ± 1.71* |
| LQC-T4 (large dosage) | 120 | 17 | 2.88 ± 1.62** | 15 | 3.20 ± 1.66 |
| LQC-T4 (small dosage) | 60 | 15 | 3.6 ± 1.76** | 12 | 3.83 ± 1.70* |
| TMP | 37 | 14 | 2.86 ± 1.79* | 12 | 2.40 ± 2.32 |
| TMP + vanillic acid | 74 + 46 | 8 | 1.63 ± 0.92 | 5 | 3.0 ± 1.87 |

Note:
compared with the model group,
*P < 0.05,
**P < 0.01

3.2.2 Effect of the LQC-T4 on the Time of the MCAO Rats Removing the Tape

The tactile sensitivity of side forelimb and the executive ability of the fine motor movement of each ischemia group rats were tested by the time of the rats removing the tape. The tape removing time of the sham operation group rats was about 20 s while the time needed for the model group rats was longer obviously, and for each administration group, especially the LQC-T4 small dosage group and the Nimodipine group, the time of the rats removing the rape can be reduced. The results were shown in table 6.

TABLE 6 effect of LQC-T4 on the time of the MCAO rats removing the tape

| Group | Dosage (mg/kg) | n | Evaluation (3 d) (s) | n | Evaluation (7 d) (s) |
|---|---|---|---|---|---|
| sham operation group | — | 15 | 14.79 ± 10.90** | 14 | 20.24 ± 15.82** |
| Model group | — | 19 | 244.29 ± 95.46 | 13 | 221.53 ± 105.33 |
| Nimodipine group | 30 | 17 | 211.13 ± 116.65 | 16 | 183.93 ± 124.50 |
| LQC-T4 (large dosage) | 120 | 17 | 222.64 ± 104.45 | 15 | 245.95 ± 98.23 |
| LQC-T4 (small dosage) | 60 | 15 | 181.31 ± 133.40 | 12 | 175.80 ± 139.06 |
| TMP | 37 | 14 | 200.43 ± 117.81 | 12 | 211.35 ± 111.15 |
| TMP + vanillic acid | 74 + 46 | 8 | 213.74 ± 121.71 | 5 | 246.61 ± 119.38 |

Note:
compared with the model group,
*$P < 0.05$,
**$P < 0.01$ 3.2.3 Effect of LQC-T4 on the Forelimb Grip Strength of the MCAO Rats The forelimb grip strength of the rats of each administration group after the ischemia was greatly lower than that of the sham operation group. The grip strength of the rats of each LQC-T4 administration group was greatly higher than that of the modeling group after being administrated for 3 day and 7 day, and with prolongation of the administration duration, the grip strength of the rats also increased. The results were shown in table 7.

TABLE 7 effect of LQC-T4 on forelimb grip strength of the MCAO rats

| group | dosage (mg/kg) | n | Grip value (g) (3 d) | n | Grip value (g) (7 d) |
|---|---|---|---|---|---|
| sham operation group | — | 10 | 442.65 ± 62.84** | 10 | 531.44 ± 64.30** |
| Model group | — | 12 | 317.01 ± 53.81 | 6 | 285.58 ± 80.02 |
| Nimodipine group | 30 | 10 | 409.08 ± 65.13** | 9 | 393.08 ± 59.61* |
| LQC-T4 (large dosage) | 120 | 10 | 386.57 ± 42.35** | 8 | 421.68 ± 59.87** |
| LQC-T4 (small dosage) | 60 | 9 | 395.50 ± 16.88** | 6 | 468.81 ± 78.14** |
| TMP | 37 | 8 | 415.19 ± 26.81** | 6 | 434.22 ± 50.23** |
| TMP + vanillic acid | 74 + 46 | 8 | 390.84 ± 45.85** | 5 | 439.15 ± 105.44* |

Note:
compared with the model group,
*$P < 0.05$,
**$P < 0.01$

4. Conclusion

For each administration group of LQC-T4, the recovery of nerve function of rats can be improved after the cerebral ischemia, especially for the small dosage group of LQC-T4, which showed a magnificent effect on recovering the limb motor function of rats after the cerebral ischemia.

Effect Example 5

Effect of LQC-T4 on Brain Histopathologic Morphology of the Rats after the Cerebral Ischemia 1 Establishing Method of Model Animal, Administration Method The same as effect example 4

2 Taking Material and Tissue Treatment

10% chloral hydrate (0.35 g/kg) was injected into the abdominal cavity of a rat to anesthetize thereof. The thoracic cavity was cut to expose the heart fully. It was intubated through left ventricle. Firstly, it was washed with 37□ saline solution 300 ml and perfused with pre-cooled 4% paraformaldehyde phosphate buffer solution (pH 7.2). When the rat was adequately fixed and the body was stiff, the head was cut and the brain was taken rapidly. And the brain was dipped into 4% paraformaldehyde solution and fixed for 24 h. Next, it was put into tissue vacuum hydroextractor, was dehydrated with gradient ethanol, made transparent with xylene, and imbedded into paraffin. 3-5 examples were taken for each group. And then 3 mm-4 mm tissue block from chiasma opticum towards caudal end at coronal position was taken, wherein the thickness of brain slice was 3 μm.

3 Observation

The rat cortex damage after cerebral ischemia and the effect of the medicine were observed through HE staining. The expression of VEGF in the cortex infarction zone and the interference of the medicine were observed at a fixed position through immunohistochemistry SP two-step method.

4 Result 4.1 The Effect of LQC-T4 on the Remaining of the Complete Neuron of the Rat Cortex after Cerebral Ischemia The rat cortex of the sham operation group showed no pathological change and the neuron morphological structure was complete. The cortex neurons of the model group degenerated and necrosed massively. Cytomembrane and nucleus were unclear in outline and a vacuole shape arisen from the lack of many neuron nucleus and cytoplasms. Compared with model group, the LQC-T4 120 mg/kg, 60 mg/kg administration group, the Nimodipine group showed pyknosis and anachromasis of nucleus, shrinkage of the cell body, a larger amount of neurons which were distinct and complete in structure, and relatively smaller and milder area of tissues which degenerated and necrosed. And the TMP group, the TMP+ vanillic acid mechanically mixed group showed a lower level of damage compared with the model group, but the effect of these group was weaker than the LQC-T4 small dosage group.

4.2 The Effect of LQC-T4 on the VEGF Expression in the Rat Cerebral Infarction Zone As to the sham operation group, VEGF positive neurons and endothelial cells which were dyed into brownish-yellow color can been seen in cerebral cortex; as to the model group, the most of the cortex neurons were lost with a few VEGF expression; as to other administration group, a large number of neurons, gliacytes and endothelial cells expressing VEGF can be seen around the cortex infarction zone. As to LQC-T4 120 mg/kg large dosage group, 60 mg/kg small dosage group, Nimodipine group, TMP group, TMP+vanillic acid mechanically mixed group, VEGF expression was more than that of the model group. It was found by the microscope that the 120 mg/kg large dosage group and 60 mg/kg small dosage group both showed more VEGF expression than the TMP group and the TMP+vanillic acid group.

Conclusion 5.1 LQC-T4 can notably increase the number of structure-complete neurons in the cortex infarction zone of rats after ischemia and reduce the area and extent of the degeneration necrosis tissues.

5.2 LQC-T4 can notable improve the VEGF expression of the neurons, gliacytes and endothelial cells around the cortex infarction zone.

Effect Example 6

Research of LQC-T4 Function Mechanics Against the Experimental Damage of Cerebral Ischemia (the Effect of LQC-T4 on Energy Metabolism and Calcium Overload)

The first thing that appeared after the cerebral ischemia was the energy metabolism dysfunction in the body and ATP reduced evidently, which caused the electrolyte disturbance in and out of a cell. Because of the shortage of the ATP in the cell, the calcium pump effect become dysfunction, which led to the calcium overload. The calcium dependent protein kinase, phosphatidase, proteinase and endonuclease were activated, which led to the break of the cell membrane and the cell cytoskeleton, and finally led to the damage and death of the neurons.

1 Material 1.1 Experimental Animal 140 healthy SD male rats, weighing 280-300 g, provided by BeiJing Vital River Laboratories, certificate No.: SCXK (Jing) 2002-2003.

1.2 Medicine to be tested: LQC-T4, TMP, vanillic acid and Nimodipine 1.3 Experimental reagents: 0.9% physiological saline, $Ca^{2+}$—$Mg^{2+}$ enzyme kit 1.4 Experimental instruments: nylon fishing wire having a diameter of 0.25 mm, German; 722 type visible spectrophotometer, the third analytical instrument factory of ShangHai; surgical instruments, Surgical Instrument Factory Of Shanghai Medical Apparatus And Instruments CO, LTD.

2 Method 2.1 Preparation of Re-Perfuse Model of Middle Cerebral Artery Occlusion of Rat 10% chloral hydrate 0.35 g/kg was injected into the abdominal cavity of a rat to anesthetize thereof. The rat was fixed as supine position. The skin was disinfected thereof by 75% medical alcohol. It was cut right in the middle of the neck. The right common carotid artery, internal carotid artery and external carotid artery were separated and the common carotid artery and external carotid artery were ligated. The internal carotid artery was clamped with a bulldog clamp. A cut was made at the crotch of the external carotid artery and the internal carotid artery followed by releasing the bulldog clamp. The nylon wire (diameter 0.25 mm, marked at a distance of 18 mm from the head end) was inserted into the cut and the insertion was stopped when some resistance was felt. The insert depth was a little longer than 18 mm to achieve the cerebral ischemia caused by middle cerebral artery occlusion. The internal carotid artery was ligated and the nylon wire was fixed. The muscle and skin were sutured layer by layer. In sham operation group, the right common carotid artery, the external carotid artery and the internal carotid artery were only exposed and separated. The rats were conventionally raised in different cages regularly. 0.5 ml penicillin was continuously injected into every rat for three days after the surgery.

2.2 The Judgment on Whether the Model was Successful

The rat condition was evaluated after 6 h after the surgery when the rats were conscious according to the Zea Longa 5 grades evaluating method, wherein no apparent neurological symptom was evaluated as 0 point; not being able to completely stretch the left front claw was evaluated as 1 point; whirling leftward was evaluated as 2 point; leaning leftward when walking was evaluated as 3 point; having an epileptic seizure, losing consciousness and not being able to walk independently was evaluated as 4 point. The rats getting 1-3 point were selected for the subsequent experiment.

2.3 Grouping and Administration

The rats were divided into 7 groups in the experiment, that is, sham operation group, model group, Nimodipine group, LQC-T4 large dosage group, LQC-T4 small dosage group, TMP group, and TMP+Vanillic acid group. The model rats getting 1 point were distributed randomly into the model group and other administration group, while the rats getting 2 point and 3 point were distributed randomly into above 6 groups according the above method and sham operation group was not involved in the above grouping. 0.5% CMC-NA (1 ml·100 $g^{-1}$) was administrated intragastrically to the blank control group and the model group, two dosage group of 120 mg·$kg^{-1}$, 60 mg·$kg^{-1}$ were administrated intragastrically to the LQC-T4 (1 ml·100 $g^{-1}$) group, and 74 mg·$kg^{-1}$ TMP+46 mg·$kg^{-1}$ vanillitc acid (1 ml·100 $g^{-1}$) were administrated intragastrically, once per day continuously for 10 days.

2.4 Taking Material and Treatment

10% chloral hydrate 0.35 g/kg was injected into the abdominal cavity to anesthetize them after the rats were administrated for 10 days. The head was cut and the brain was taken. The cranial bones were stripped, the meninges were peeled off to separate the ischemia side of the brain, the blood streak was striped and then the brain was weighed. 4 times amount of 0.9 physiological saline was added and the brain was homogenized in 0° C. ice bath. For part of the homogenized sample, it was centrifugalized for 15 min at 4° C. and the supernatant liquid was placed into a 0.8 ml EP tube and then the tube was stored into −20° C. fridge to be tested; for part of the homogenized sample, a proper amount of physiological saline was further added into it so as to dilute it into 10%, 2%, 1% homogenate, then the homogenate was centrifugalized for 15 min at 4° C. at 4000 rpm and the supernatant liquid was placed into a 0.8 ml EP tube and the tube was stored into −20° C. fridge to be tested.

2.5 Index Detection

It was detected with 722 type visible spectrophotometer according to the kit operation.

2.6 Statistical Method

Statistical treatment: the SAS 8.2 statistical software was used to carry out the one-way ANOVA variance analysis and the difference among the groups were compared by t-test.

3 Result 3.1 Effect of LQC-T4 on $Ca^{2+}$—$Mg^{2+}$ ATPase of MCAO Rats

The activity of $Ca^{2+}$—$Mg^{2+}$ ATPase increased notably after the ischemia. The Nimodipine group, the LQC-T group and the TAM group all can improve the activity of the $Ca^{2+}$—$Mg^{2+}$ ATPase in the ischemia rats while TMP+vanillic acid mechanically mixed group were not statistically different from model group. The results were shown in table 8.

TABLE 8 effect of LQC-T4 on $Ca^{2+}$—$Mg^{2+}$ ATPase of MCAO rats

| Group | dosage (mg/kg) | n | Ca—Mg ATPase activity |
|---|---|---|---|
| sham operation group | — | 15 | 3.66 ± 1.29* |
| Model group | — | 12 | 5.32 ± 2.61 |
| Nimodipine | 30 | 14 | 13.25 ± 5.73** |
| LQC-T4 (large dosage) | 120 | 13 | 10.07 ± 5.15* |
| LQC-T4 (small dosage) | 60 | 14 | 8.91 ± 4.05* |
| TMP | 37 | 9 | 9.13 ± 4.11* |
| TMP + vanillic acid | 74 + 46 | 5 | 5.01 ± 3.85 |

Note:
compared with the model group,
*P < 0.05,
**P < 0.01

4 Conclusion

The large dosage and the small dosage groups of LQC-T4 both can increase the activity of $Ca^{2+}$—$Mg^{2+}$ ATPase notably.

Effect Example 7

Research of LQC-T4 Function Mechanics Against the Experimental Cerebral Ischemia Damage ii (the Effect of LQC-T4 on Oxidative Stress Damage)

When the cerebral ischemia and anoxia happened, a large amount of free radicals were generated, which acted on multivalent unsaturated fatty acid, reacted with protein, saccharide and phospholipid etc. of the active cells, led to the crosslink and oxidation of the molecules and the polymerization and degradation of the polysaccharide molecules. Especially the peroxidation of the membrane phospholipid resulted in destroying the completeness of the membrane structure and the subcellular structure, and the increase of membrane permeability with the lack of the function and causing the death of cells. The oxygen radicals can activate PLA2, break the balance of TXA2/PGI2, increase the content of TXA2 in ischemic zone and penumbra zone and thus lead to the angiospasm and intravascular coagulation and aggravate the ischemic damage.

1 Material 1.1 Experimental animal: the same as effect example 6

1.2 Medicine to be tested: the same as effect example 6

1.3 Experimental reagents: 0.9% physiological saline, SOD kit, MDA kit.

1.4 Experimental instruments: the same as effect example 6

2 Method: the same as effect example 6

3 Result 3.1 Effect of LQC-T4 on SOD of the MCAO Rats

The SOD activity of the model group after the ischemia reduced notably compared with the sham operation group while every administration group can greatly improve the SOD activity. The results were shown in table 9.

TABLE 9 effect of LQC-T4 on SOD of MCAO rats

| Group | Dosage (mg/kg) | n | SOD |
|---|---|---|---|
| sham operation group | — | 14 | 61.85 ± 12.53** |
| Model group | — | 9 | 40.28 ± 7.51 |
| Nimodipine | 30 | 12 | 79.85 ± 36.57** |
| LQC-T4 (large dosage) | 120 | 10 | 85.03 ± 56.03* |
| LQC-T4 (small dosage) | 60 | 13 | 75.29 ± 30.08** |
| TMP | 37 | 8 | 61.58 ± 16.23** |
| TMP + vanillic acid | 74 + 46 | 5 | 90.18 ± 19.58** |

Note:
compared with the model group,
*P < 0.05,
**P < 0.01

3.2 Effect of LQC-T4 on MDA of the MCAO Rats

The MDA content of the model group rats increased compared with the sham operation group rats after the ischemia while the LQC-T4 large dosage group rats and the TMP+vanillic group rats reduced the MDA content but showed no statistical difference from the model group rats. The results were shown in table 10.

TABLE 10 effect of LQC-T4 on MDA of MCAO rats

| Group | Dosage (mg/kg) | n | MDA |
|---|---|---|---|
| sham operation group | — | 10 | 10.90 ± 4.54 |
| Model group | — | 9 | 14.53 ± 3.29 |
| Nimodipine | 30 | 9 | 13.70 ± 6.56 |
| LQC-T4 (large dosage) | 120 | 6 | 11.08 ± 4.53 |
| LQC-T4 (small dosage) | 60 | 9 | 14.32 ± 6.31 |
| TMP | 37 | 5 | 13.27 ± 3.96 |
| TMP + vanillic acid | 74 + 46 | 5 | 10.07 ± 3.49 |

4 Conclusion

The large dosage group and the small dosage group of LQC-T4 both can improve the activity of the SOD and MDA enzyme of the ischemia rats.

Effect Example 8

Research of LQC-T4 Function Mechanics Against the Experimental Cerebral Ischemia Damage III (the Effect of LQC-T4 on VEGF)

VEGF showed the direct neuroprotective effect on hypoxia, excitotoxicity and oxidative stress. Second, the blood flow stored in the new vessel which is generated by the VEGF was provided for the neurons of the ischemic penumbra zone, and it was found that new vessels was generated in the cerebral ischemia zone of the apoplexy patient, and the more the new vessels generated, the longer the patient lived. VEGF also can promote the neurogenesis induced by the ischemia.

1 Material 1.1 Experimental animal and 1.2 Medicine to be tested: the same as effect example 6

1.3 Experimental reagents: PBS, VEGF kit 1.4 Experimental instruments: nylon fishing wire having a diameter of 0.25 mm, German; enzyme-labeling instrument (Finland, Thermo BioAnalysis Company's product, Multiskan MK3 model); surgical instruments, Surgical Instrument Factory of Shanghai Medical Apparatus And Instruments CO, LTD.

2. Method 2.1 The preparation of re-perfusion model of middle cerebral artery occlusion of a rat: the same as effect example 6

2.2 The judgment on whether the model was successful and 2.3 Grouping and administration: the same as effect example 6

2.4 Taking Material and treatment: the same as effect example 6

2.5 Index Detection

As to VEGF, it is detected using enzyme-labeling instrument at 450 nm according to the kit.

2.6 Statistical Method

Statistical Treatment:

The SAS 8.2 statistical software was used to carry out the one-way ANOVA variance analysis and the differences among the groups were compared by t-test.

3 Result: the effect of LQC-T4 on the contents of VEGF of MCAO rats

The VEGF content of the model group rats notably reduced compared with the sham operation group rats after the ischemia ($P<0.05$), and LQC-T4 small dosage group rats and TMP group rats can improve the VEGF content ($P<0.05$) notably. The results were shown in table 11.

TABLE 11

VEGF activity comparison of MCAO rats

| Group | Dosage (mg/kg) | n | VEGF |
|---|---|---|---|
| sham operation group | — | 9 | 28.14 ± 10.98* |
| Model group | — | 9 | 18.28 ± 1.62 |
| Nimodipine | 30 | 9 | 19.66 ± 2.34 |
| LQC-T4 (large dosage) | 120 | 8 | 22.86 ± 8.42 |
| LQC-T4 (small dosage) | 60 | 9 | 25.67 ± 9.69* |
| TMP | 37 | 5 | 23.62 ± 6.68* |
| TMP + vanillic acid | 74 + 46 | 5 | 21.17 ± 7.08 |

Note:
compared with the model group,
*$P < 0.05$,
**$P < 0.01$

4 Conclusion

The LQC-T4 small dosage group can increase the VEGF content of the MCAO rats.

Toxicity Example

Toxicity Example 1

1. Experimental Project: Acute Toxic Experiment of Mice by Oral Administration

2. Experimental Material:

ICR white mice (half female and half male, 18-22 g, experiment animal certificate No.: SCXK (Jing) 2006-0009);
LQC-T4 (white powder (self made); and LQC-T4 4500 mg was dissolved into 0.5% sodium carboxymethyl cellulose 100 ml and then suspended by supersonic wave. The suspension was used in situ).

3. Experimental Method:

The qualified animals were quarantined and weighed before the administration. The animals were divided into groups randomly by weight. The intragastric administration tool was used for mice to carry out the intragastric administration. The mice were fasted but not water-deprived (continuously for 14 h) overnight before being administrated. The mice were administrated at 9:00 AM for the first time (1800 mg/kg) on the present administration day and observed continuously for 1 h. The mice were administrated for the second time (1800 mg/kg) at an interval of 6 h since the first administration and observed continuously for 1 h. The mice were administrated for the third time (1800 mg/kg) at an interval of 6 h since the second administration, observed continuously for 1 h and then the mice were fed.

4. Experiment Results:

No death was observed in 12 h after the administration. The death condition of each group mice in 14 days was shown in the following table.

TABLE 12 summary of the regular observation results of the mice acute toxic experiment of LQC-T4 by oral administration

| group | sex | Number of animal | Animal reaction in 14 days after the administration | | | | | | |
|---|---|---|---|---|---|---|---|---|---|
| | | | appearance | behavior | hair | respiration | posture | reaction | death |
| Control group | ♂ | 10 | ✓ | ✓ | ✓ | ✓ | ✓ | ✓ | 0 |
| | ♀ | 10 | ✓ | ✓ | ✓ | ✓ | ✓ | ✓ | 0 |
| LQC-T4 | ♂ | 10 | ✓ | ✓ | ✓ | ✓ | ✓ | ✓ | 0 |
| | ♀ | 10 | ✓ | ✓ | ✓ | ✓ | ✓ | ✓ | 0 |

Note:
✓ means normal.

1. Summary

In the present mouse acute toxic experiment of LQC-T4 by oral administration, the maximum dosage of 5400 mg/kg was administrated to the mice and observed continuously for 14 days. No toxic reaction was observed within 14 days, which meant that the safety of this medicine was high.

Formulation Example

Formulation Example 1

LQC-T4 10 g was taken and then proper injection (including freeze-dry powder injection and aseptic powder injection) excipients (distilled water, polyethylene glycol) were added thereinto. An antitumor injection was prepared according to the common injection (including freeze-dry powder injection and aseptic powder injection) preparing technology.

Formulation Example 2

LQC-T4 10 g was taken and then proper tablet (including extended action tablet, matrix tablet, coated tablet, dispersible tablet, etc.) excipients (starch, sodium carboxymethylcellulose) were added thereinto. An antitumor tablet was prepared according to the common tablet (including extended action tablet, matrix tablet, coated tablet, dispersible tablet, etc.) preparing technology.

Formulation Example 3

LQC-T4 10 g was taken and proper capsule excipients (starch, dextrin) were added thereinto. An antitumor capsule was prepared according to the common capsule preparing technology.

Formulation Example 4

LQC-T4 10 g was taken and proper emulsion (including micro emulsion, nano emulsion, etc.) excipients (polylactic acid) were added thereinto. An antitumor emulsion (including micro emulsion, nano emulsion, etc.) was prepared according to the common emulsion preparing technology.

Formulation Example 5

LQC-T4 10 g was taken and proper granule excipients (starch, cyclodextrin) were added thereinto. An antitumor granule was prepared according to the common granule preparing technology.

Formulation Example 6

LQC-T4 10 g was taken and proper sustained release formulation excipients (sodium carboxmethylcellulose, microcrystalline cellulose) were added thereinto. An antitumor sustained release formulation was prepared according to the common sustained release formulation preparing technology.

Formulation Example 7

LQC-T4 10 g was taken and proper oral liquid excipients (distilled water, sucrose) were added thereinto. An antitumor oral liquid was prepared according to the common oral liquid preparing technology.

Formulation Example 8

LQC-T4 10 g was taken and proper liposome formulation excipients (lecithin, cephalin) were added thereinto. An antitumor liposome formulation was prepared according to the common liposome formulation preparing technology.

Formulation Example 9

LQC-T 10 g was taken and proper injection (including freeze-dry powder injection and aseptic powder injection) excipients were added. An antitumor injection was prepared according to the injection preparing technology.

Formulation Example 10

LQC-T 10 g was taken and proper tablet (including extended action tablet, matrix tablet, coated tablet, dispersible tablet, etc.) excipients were added thereinto. An antitumor tablet was prepared according to the tablet (including extended action tablet, matrix tablet, coated tablet, dispersible tablet, etc.) preparing technology.

Formulation Example 11

LQC-T 10 g was taken and proper capsule excipients were added thereinto. An antitumor capsule was prepared according to the capsule preparing technology.

Formulation Example 12

LQC-T 10 g was taken and proper emulsion (including micro emulsion, nano emulsion, etc.) excipients were added thereinto. An antitumor emulsion (including micro emulsion, nano emulsion, etc.) was prepared according to the emulsion preparing technology.

Formulation Example 13

LQC-T 10 g was taken and proper granule excipients were added thereinto. An antitumor granule was prepared according to the granule preparing technology.

Formulation Example 14

LQC-T 10 g was taken and proper sustained release formulation excipients were added thereinto. An antitumor sustained release formulation was prepared according to the sustained release formulation preparing technology.

Formulation Example 15

LQC-T 10 g was taken and proper oral liquid excipients were added thereinto. An antitumor oral liquid was prepared according to the oral liquid preparing technology.

Formulation Example 16

LQC-T 10 g was taken and proper liposome formulation excipients were added thereinto. An antitumor liposome formulation was prepared according to the liposome formulation preparing technology.

We claim:
1. A compound LQC-T having the following formula:
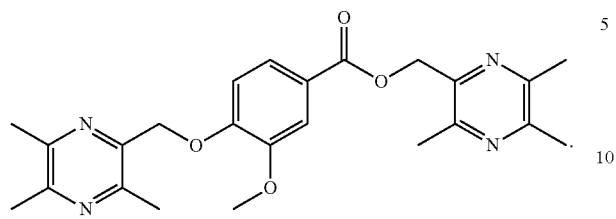
2. A method of making the compound according to claim 1, comprising: dissolving vanillic acid into an organic solvent to react with bromotetramethylpyrazine in the presence of a catalyst to form compound LQC-T.
* * * * *